Figure 4:
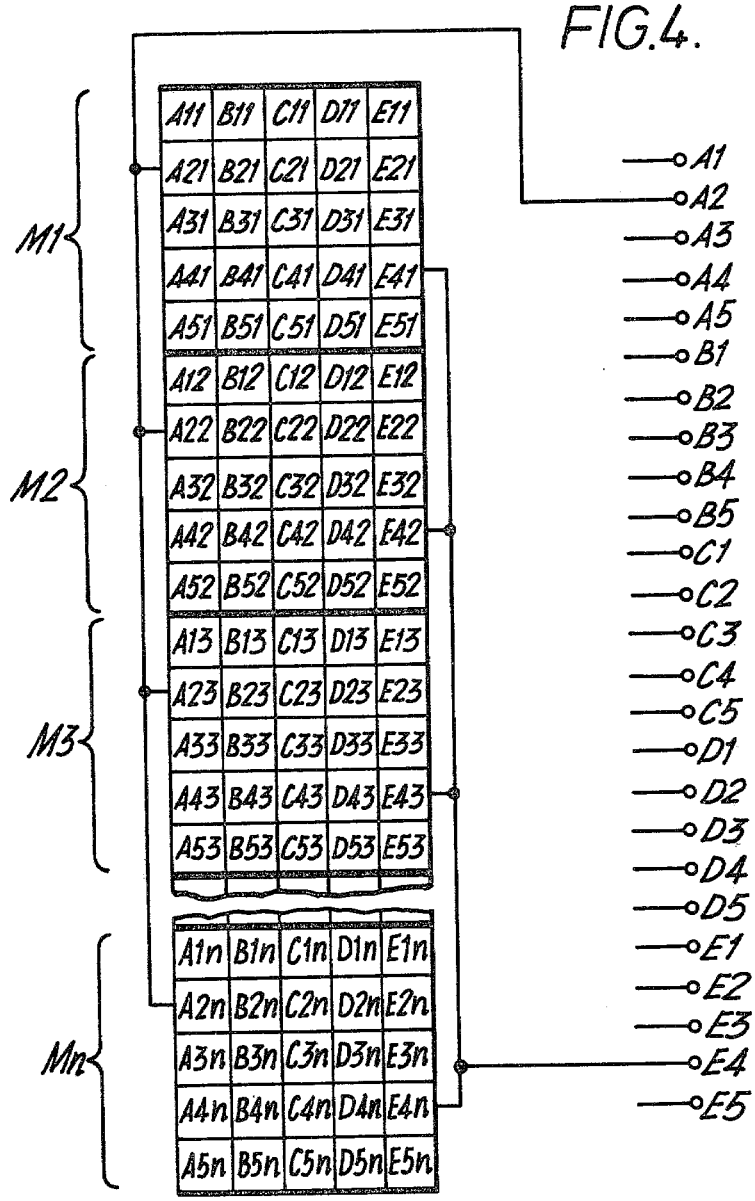

United States Patent [19]

Tailleur et al.

[11] 4,338,028

[45] Jul. 6, 1982

[54] APPARATUS FOR INSPECTING TRANSLUCENT ARTICLES FOR FAULTS

[75] Inventors: André Tailleur, Gennevilliers, France; Brendan F. O'Connor, Dublin, Ireland

[73] Assignees: Udaras Na Gaeltachta, Furbo, Ireland; Societe Generale pour l'Emballage, Paris, France

[21] Appl. No.: 124,020

[22] Filed: Feb. 25, 1980

[30] Foreign Application Priority Data

Feb. 26, 1979 [IE] Ireland .................................. 320/79

[51] Int. Cl.³ ............................................ G01N 21/90
[52] U.S. Cl. ................................ 356/240; 250/223 B; 356/428
[58] Field of Search ............... 356/239, 240, 428, 430, 356/431; 250/223B, 553, 562, 563, 572, 578

[56] References Cited

U.S. PATENT DOCUMENTS 3,529,169  9/1970  Heaney et al. .................. 356/428 X
3,987,301 10/1976  O'Connor ....................... 356/240 X
4,165,939  8/1979  Woodrow et al. ............. 250/572 X

OTHER PUBLICATIONS

Bratland, "Modular Matrix Photodetector", *IBM Tech. Disc. Bull.* vol. 13, No. 3, p. 699, 8/70.

Primary Examiner—John K. Corbin
Assistant Examiner—Matthew W. Koren

Attorney, Agent, or Firm—Sughrue, Mion, Zinn, Macpeak and Seas

[57] ABSTRACT

This invention concerns an apparatus for detecting the presence of faults in a translucent container of the kind comprising a scanning zone in which a translucent container is rotated while being repeatedly scanned by a spot beam of light in a direction parallel to the axis of rotation of the container, a light collection apparatus being arranged to receive light from the beam after passing through the container.

The light collection apparatus comprises a rectangular matrix of photosensitive devices disposed behind a light-diffusing screen upon whose front surface the light from the scanning beam falls after passing through the container. A rectangular grid of thin white walls is sandwiched between the screen and the photosensitive devices so as to define a plurality of boxes with a respective device being located at the rear of each box. The grid thus effectively divides the screen into a large number of elemental areas and provides that each device receives light substantially only from a respective elemental area of the screen.

This invention permits the detection of certain nonocclusive refraction faults in the translucent container by selective examination of the device outputs, as well as the detection of occlusive faults by measurement of the total light falling on the screen.

11 Claims, 14 Drawing Figures

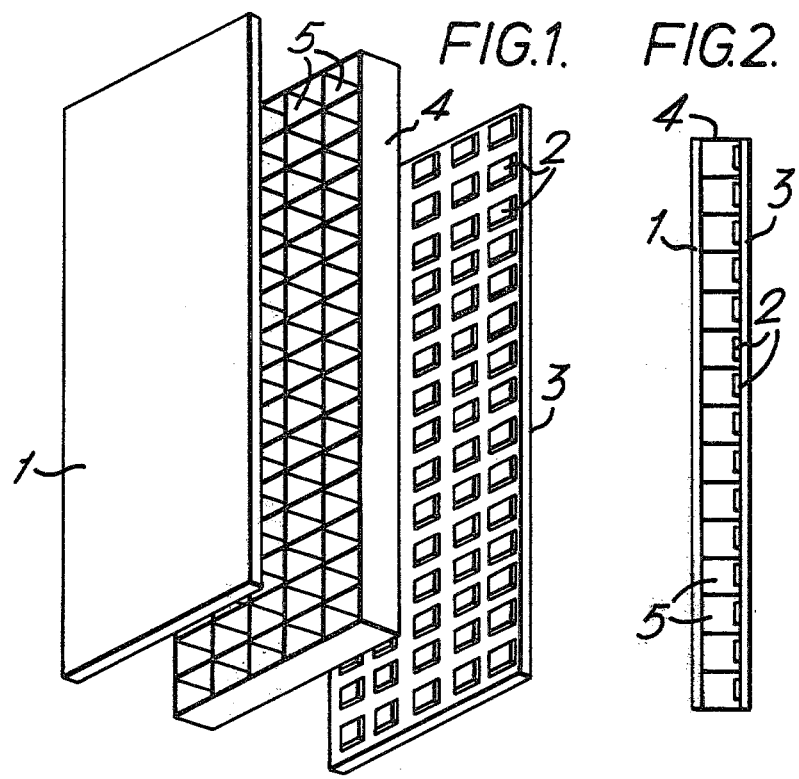
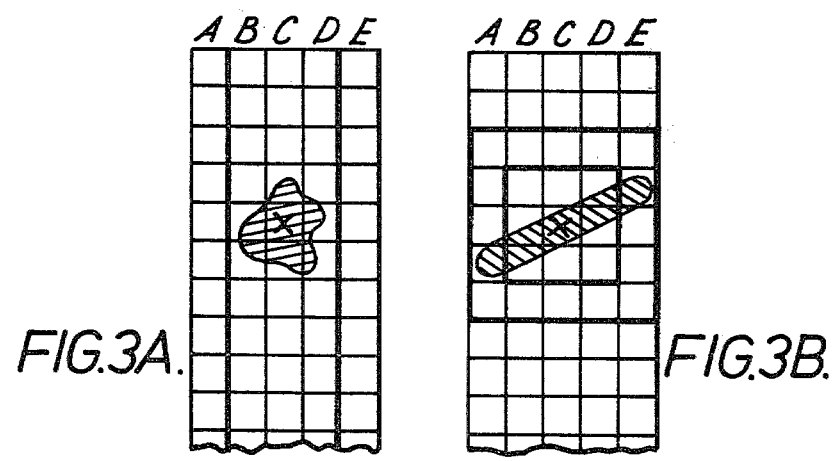

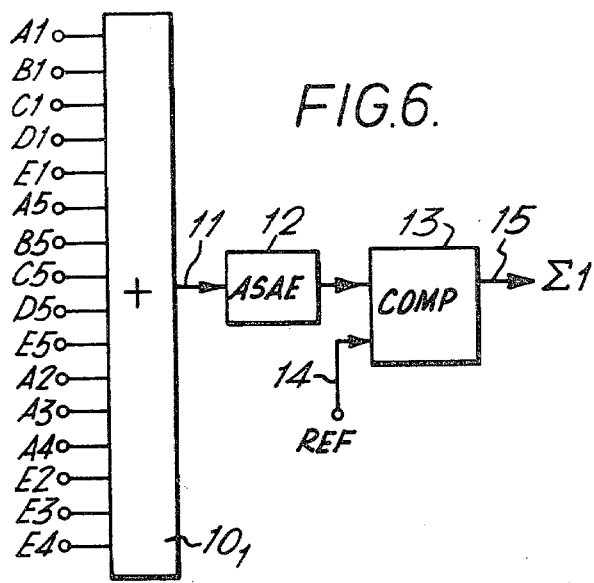

APPARATUS FOR INSPECTING TRANSLUCENT ARTICLES FOR FAULTS

This invention relates to an apparatus for detecting the presence of faults in translucent articles, particularly containers such as bottles.

The bottle inspection apparatus described in Irish Patent Specification No. 31613 and British Patent Specification No. 1,430,547 comprises a light source projector system for producing a concentrated ribbon of light. The ribbon of light is projected onto a rotating drum which tangentially supports twenty outwardly reflecting plane silvered mirrors. The drum is driven by an electric motor and associated gear, the ribbon of light impinges upon the rotating mirrors and is reflected downwardly through an aperture in the floor of a casing to a number of plane mirrors thereby providing a repetitive scanning ribbon of light. The reflected ribbon of light is further reflected from these three plane mirrors which are angularly mounted within a vertically disposed column located below the casing. A rotating table encircles the column which has a vertical slot permitting exit of the further reflected ribbon of light from the column. Supported by the rotating table is a vertical masking member having a vertical slit which serves to occlude all but portion of the repetitive ribbon of light thereby concentrating the latter into a narrow spot beam of light which passes through an angle of approximately twenty degrees as the table and slit are rotated. Thus the concentrated spot beam of light, hereinafter referred to as the scanning beam, scans through an angle in the vertical plane and moves through an angle in a horizontal plane. A translucent container or bottle to be inspected is carried around the periphery of the rotating table by fingers serving to press the bottle against rotating rollers which revolve the bottle as it passes through the scanning zone penetrated by the concentrated scanning beam the latter being focused substantially on the axis of the bottle. Light passing through the bottle is collected by a light collection apparatus, associated with a photo-multiplier tube which feeds the resulting scan signal to a control circuit. The light collection apparatus may be a number of glass or plastics fibre optic elements mounted in a matrix arrangement on the front surface of a platform. The other ends of the fibres are taken together to form a bundle the end face of which is suitably shaped, optically polished and optically coupled to a photosensor element namely the photo-multiplier tube.

It will be appreciated that during the scanning period the scanning beam passing through the masking slit continuously scans in a vertical plane simultaneously as it is caused to move in a horizontal plane by rotary movement of the masking member. Further, the bottle is continuously rotated during transit hereof through the scanning zone and the scanning rate is so arranged that the entire area of the bottle is overscanned by 25%.

This original apparatus used the combination of fibre-optics and a photo-multiplier tube to determine the total light incident upon the light collecting screen, since many defects in the bottle caused diffusive or refractive propagation of the beam away from the single scanning point, and since these did not represent occlusions or dirt in the bottle but more often than not were part of lettering or other ornamentation on the container the light coming through had to be collected in total in order to see if there was any occlusive fault.

The first limitation on this system is the significant inefficiency of the terminal end of the fibres themselves where they come out into the matrix. By their very definition these have not particularly efficient light collecting properties, since they terminate in an optically random fashion in the air and have a comparatively narrow angle of acceptance. Their subsequent transmission to the face of the photo-multiplier tube is a further source of loss, and whilst photo-multiplier tubes themselves are highly efficient they are also equally efficient in the amplification of noise.

In addition it was found that manufacturers of hollow glassware wished on many occasions to detect faults which were not occlusive, such as folds, halos, bubbles and deformaties within the bottle. Since these particular defects had virtually no occlusive properties the system was incapable of resolving them.

The present invention is directed towards overcoming the above disadvantages of the prior art container inspection apparatus, although in its broadest aspect the invention is of more general applicability.

According to the present invention there is provided an apparatus for detecting the presence of faults in an article of translucent material, the apparatus comprising means for generating a spot beam of light and causing it to repeatedly scan in a first direction, means for transporting the translucent material of the article past the spot beam of light in a second direction non-parallel to the first direction so that the surface of the translucent material is repeatedly scanned by the beam in a direction non-parallel to the direction of motion of the material, a light collection apparatus arranged to receive light from the beam after passing through the translucent material, the light collection apparatus comprising a light-diffusing screen having a front surface positioned to receive light from the translucent material and a rear surface facing a matrix of photosensitive devices each arranged to provide an electric output signal dependant upon the amount of light emerging substantially only from the rear surface of a respective elemental area of the screen, and electrical circuit means for processing the output signals of the photosensitive devices produced during scanning of the material to detect faults in the article.

In its application to the inspection of translucent containers, the invention provides an apparatus for detecting the presence of faults in translucent containers, the apparatus comprising a scanning zone, means for rotating a translucent container within the scanning zone, means for generating a spot beam of light and causing it to repeatedly scan a container in the scanning zone in a direction parallel to the axis of rotation of the container, a light collection apparatus arranged to receive light from the beam after passing through the container, the light collection apparatus comprising a light-diffusing screen having a front surface facing in a direction to receive light from the scanning zone and a rear surface facing a matrix of photosensitive devices each arranged to provide an electric output signal dependant upon the amount of light emerging substantially only from the rear surface of a respective elemental area of the screen, and electrical circuit means for processing in at least two ways the output signals of the photosensitive devices produced during scanning of the container, on the one hand to detect occlusive faults and on the other hand by selective examination to detect substantially non-occlusive refractive faults.

Preferably the matrix of photosensitive devices is a rectangular matrix with one of the major axis thereof arranged parallel to the axis of rotation of the container, and the light collector further includes a rectangular grid of thin walls sandwiched between the screen and the matrix so as to define a plurality of boxes with a respective photosensitive device located at the rear of each box.

Figure 5:
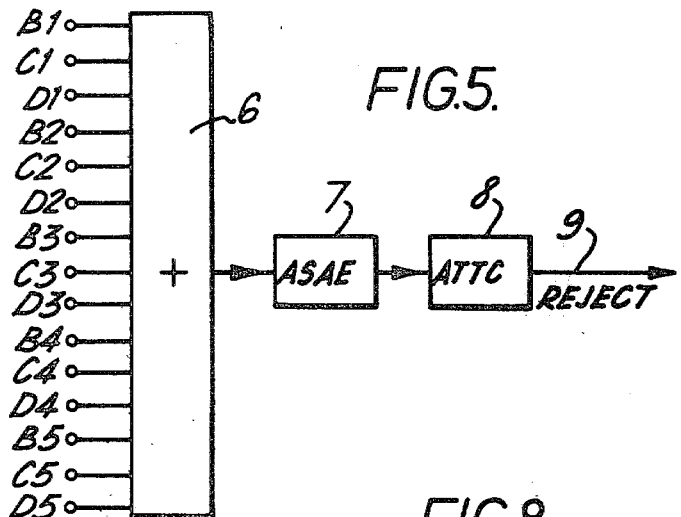
Figure 8:
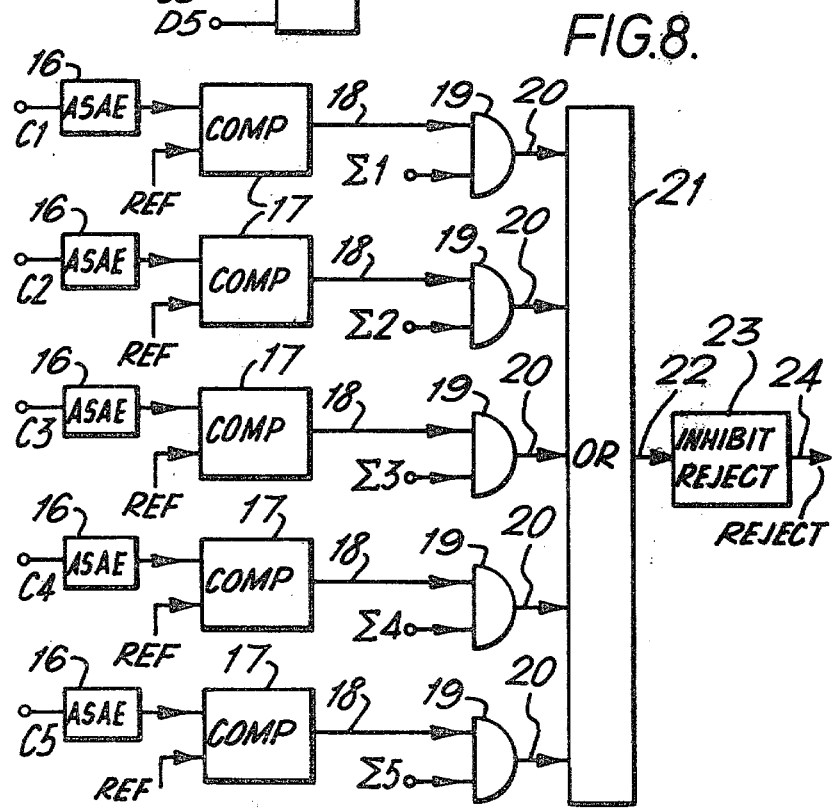
Figure 7A:
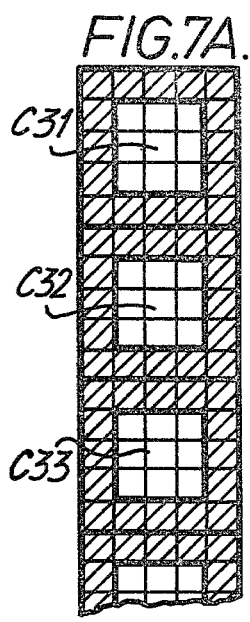
Figure 7B:
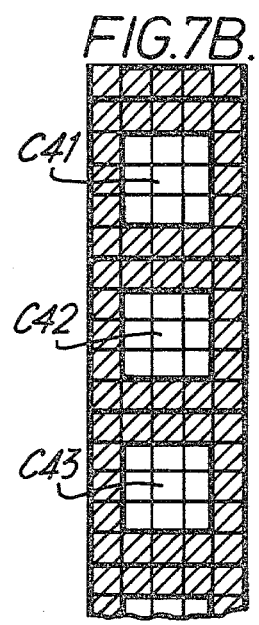
Figure 7C:
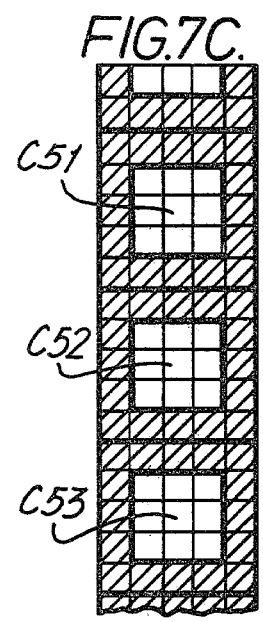
Figure 7D:
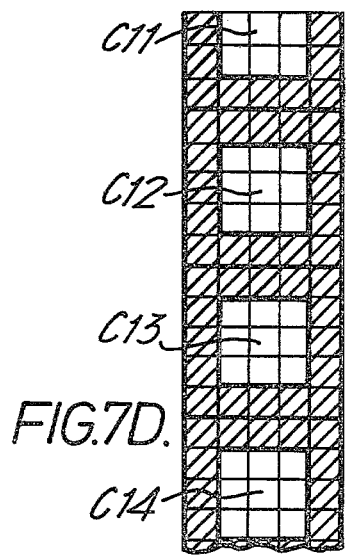
Figure 7E:
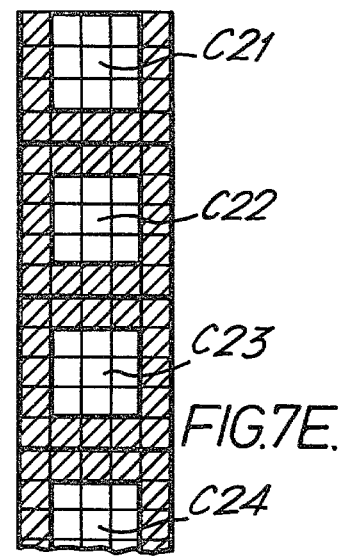

An embodiment of the invention will now be described, by way of example, with reference to the accompanying drawings, in which:

FIG. 1 is an exploded view of a light collector used in an embodiment of a bottle inspecting apparatus according to the present invention, FIG. 2 is a cross-sectional view of the light collector when assembled for use, FIGS. 3A and 3B illustrate two typical patterns of light which may fall on the light collector after passage of a scanning beam through a bottle being inspected, FIG. 4 illustrates how the individual photodiodes of the light collector are interconnected, FIG. 5 is a block schematic diagram of a circuit for detecting occlusive faults in a bottle being inspected, FIG. 6 is a block schematic diagram of one of five similar circuits for detecting significant refractive faults in a bottle being inspected, FIG. 6A is a table showing the respective combinations of inputs to the other four circuits similar to that of FIG. 6, FIGS. 7A to 7E illustrate the different combinations of photodiodes to which the five circuits similar to FIG. 6 are responsive respectively, and FIG. 8 is a block schematic diagram of a circuit for selecting the output of the appropriate one of the five circuits similar to FIG. 6 in accordance with the position of the scanning beam.

The inspection apparatus of the present embodiment may use basically the same scanning arrangement as that used in the inspection apparatus described in the aforementioned Irish Patent Specification No. 31613 and British Patent Specification No. 1,430,547, and will therefore not be described in detail here. However, the present scanning arrangement differs from the previous arrangements in that, while being rotated and repeatedly vertically scanned in the scanning zone by the scanning beam focussed on its axis, the bottle is not subject to movement through an angle in the horizontal plane as in the previous arrangement, but is held stationary. As will become clear, this is because the present embodiment requires that the nominal position of the scanning beam when striking the light collector after passing through the bottle should follow the same predetermined vertical path on the light collector for all vertical scans of the bottle. If the bottle and scanning beam were moved horizontally during the vertical scanning this would clearly require a further compensating means. Thus for the present embodiment the prior scanning arrangement is modified so that the table carrying the bottle to be inspected is temporarily halted while rotation and vertical scanning of the bottle takes place. This is a modification well within the capabilities of one skilled in the art. Furthermore, in the present embodiment the scanning beam of light may be a laser beam.

The main difference between the present embodiment and the prior inspection apparatus lies in the construction of the light collector and the method of processing the electrical signals produced thereby. Dealing first with the light collector, FIG. 1, this comprises a light-diffusing translucent screen 1 at the front, a rectangular matrix of photodiodes 2 at the rear mounted on a printed circuit board 3, and intermediate the screen 1 and board 3 a rectangular grid or honeycomb 4 of thin opaque white walls defining a matrix of square boxes 5 open at the front and rear respectively and having a periodicity the same as that of photodiodes 2. The light collector is shown in exploded view in FIG. 1, but when assembled for use the grid 4 is closely sandwiched between the screen 1 and board 3, so as to substantially prevent any leakage of light from one box to another within the structure, with a respective diode 2 located centrally within the rear end of each box 5. This is shown in cross-section in FIG. 2.

In use the light collector is positioned vertically with the screen 1 facing the inspection zone of the apparatus such that the scanning spot beam of light nominally travels down the centre of the light collector after passing through the rotating bottle being scanned. In the present embodiment the matrix of diodes is 5 diodes wide and has a depth determined by the height of the bottle or part thereof to be inspected. In this case, therefore, the scanning beam nominally travels down the centre column of the five columns of boxes, striking the screen 1 over each centre box 5 in turn. For simplicity, FIG. 1 only shows a matrix 15 diodes in depth.

Although in the ideal case (perfectly smooth and regular bottle) the scanning beam will travel only down the centre column of boxes, in practice due to scattering or refraction (as a result of faults, lettering, ornamentation, etc) and the diffusive effect of the screen 1, the beam, as it strikes each box, will produce on the screen a pattern of light which generally extends beyond the boundary of the box. Thus, referring to FIG. 3A, when the spot beam is directed nominally at the box X after passing through the bottle a pattern such as that shown in hatched lines will typically be produced, although the light from the bottle will still predominantly fall on the nominal box X except in the case of gross deformation of the bottle. The purpose of the particular construction of light collector described above is to permit a degree of analysis of the patterns produced by the light impinging on the translucent screen 1, and in particular to permit differentiation between those patterns which are produced by serious refractive faults warranting rejection of the bottle, and those patterns which are produced by minor refractive faults (or lettering or ornamentation) which can be accepted. The light collector is also designed to permit the detection of occlusive faults.

The light collector operates as follows. As will be described, the patterns are detected by examining the outputs of selected photodiodes at each stage of the scanning, and in order to provide maximum sensitivity for this purpose it is desirable that each diode produce as large a signal as possible. This is achieved by each diode being surrounded as previously described by a respective box 5 which effectively allocates to that diode a respective elemental area of screen 1 from which only that diode and no other can receive light. Because the white walls cause most of the light diffusing through the screen into a given box to be re-radiated onto the photodiode, the latter responds to substantially the total light emerging into the box from its allocated area of the screen 1. The result is a substantially higher output from each diode, for a given pattern, than if the grid 4 were absent. Furthermore, the walls of the boxes substantially prevent "spillover" of light from one box to the next so that the signals from adjacent diodes may be sharply differentiated, each responding only to the light emerging from its own portion of the screen. If the honeycomb or grid 4 were absent the signal differentiation between one diode and the next would be much less making it much more difficult to differentiate between different types of patterns.

The dimensions of the light collector and its distance from the bottle being scanned are determined by the diameter of the bottle and its expected scattering characteristics (taking into account any lettering or ornamentation) in such manner that, for bottles of acceptable quality, during each vertical scan the pattern of light falling on the screen 1 at no time extends substantially beyond the B, C and D columns of boxes, FIG. 3A. Furthermore, any refractive faults (such as hammer finish) which do not cause the pattern to fall onto the A or E columns are assumed to be of a minor nature and therefore acceptable. Occlusive faults such as dirt in the bottle may therefore simply be detected by summing the total output from all the diodes in the B, C and D columns (i.e. within the heavy lines) and comparing the sum with a reference threshold appropriate to the portion of the scan concerned. When the sum signal drops below the threshold an occlusive defect is assumed to be present resulting in the generation of a reject signal. Circuitry for performing the B, C and D column summing will be described later, although it is to be understood that since the detection of occlusive defects is concerned only with the sum total of the light and not its distribution the summing could be performed over all five columns A to E. It should be pointed out that for accuracy of summing the thickness of the screen 1 should be such that the diffusion introduced by the screen is sufficient to substantially eliminate the occlusive effect of the walls of the boxes 5 on the laser beam. A typical embodiment of screen 1 is 4 mm of "030 Opal Perspex".

Clearly the B, C and D column summing is capable of detecting major non-occlusive refractive faults also, if these are sufficient to shift the bulk of the pattern over towards the A or E column to an extent which will cause such a drop in the B, C, D column sum signal as to be detectable by the threshold comparison. However, some non-occlusive refractive faults, while being serious enough to warrant rejection of the bottle, do not cause a sufficiently large drop in the B, C, D column sum signal as to bring it below the threshold, and so cannot be detected by this means.

One example of such a fault is the fold. A fold in container terminology is a line defect on the surface of the container and the laser beam when striking this produces a pattern quite different from that produced when the beam passes through good glass. The pattern is a long line say 30 mm wide on the opal screen 1 at right angles to the direction of the fold at the point of intersection with the beam. Such a pattern is shown in FIG. 3B, extending into the A and E columns. However, the amount of light deflected into the A and E columns by the fold is usually quite small, often below 10% of the total from the beam and sometimes as low as 2%, and it is not practical to detect such faults by the drop in amplitude of the B, C, D column sum signal as the comparison threshold for this sum signal would have to be set so high as to also reject perfectly good bottles due to natural and acceptable variations in transmission properties. Furthermore, there would be no drop in the B, C, D column sum signal at all if the line pattern lay generally vertically wholly within the B, C and D columns, and in such case the fold would be impossible to detect in any case.

The solution to this problem is to examine a 5×5 frame of boxes centred on the current nominal box X in the C column at which the spot beam emerging from the bottle is directed. This 5×5 frame is shown in heavy lines in FIG. 3B. We have determined that the scanning laser beam is normally only scattered into this frame when a fold or suchlike defect is scanned, and remains substantially wholly within the 3×3 array bounded by the frame when the portion of the bottle scanned is of acceptable quality. By summing the outputs of the diodes in the frame a sum signal may be produced corresponding to the total amount of light falling on the frame. This sum signal can be compared with a frame threshold level and when the threshold is exceeded a reject signal generated. The advantage of this arrangement is that the frame threshold level can be set quite low so as to detect the small amounts of light falling in the frame due to a fold and which could not be detected by the drop in the B, C, D column summation. Since a fold can occur anywhere in a vertical scan, clearly the frame has to be "stepped" vertically down the diode matrix in synchronism with the scanning beam so as always to be centred on the current nominal box X in the C column. Circuitry to perform the frame summation, comparison and stepping will be described later.

In order to simplify the signal processing circuitry the diodes of the matrix are interconnected in a particular manner, as shown in FIG. 4. The diode matrix is notionally divided into a series of adjacent 5×5 sub-matrixes M1, M2, M3 . . . Mn and the diodes having the same relative position in each sub-matrix are connected together to provide a common output. Thus, for example, diodes A21, A22, A23 . . . A2n are connected together as shown to a common output A2, diodes E41, E42, E43 . . . E4n are connected together to a common output E4, and so on. The result is 25 output terminals A1 . . . E5 as shown on the right of FIG. 4 each connected to that diode in each sub-matrix identified by the same two initial characters. The connections between the diodes are made on the printed circuit board 3. Before further processing, the signals on the outputs A1 to E5 are amplified by means not shown, and in the following description the designations A1 to E5 will be used to identify the amplified signals derived from the similarly designated output terminals of the matrix.

The B.C.D. column summation and comparison is performed by the circuit shown schematically in FIG. 5. All the signals from the B, C and D output terminals of the diode matrix are added together in an adder 6 to provide a sum signal corresponding to the total amount of light falling on the B, C and D columns of the matrix. The sum signal is applied in known manner to an Automatic Signal Ammplitude Equalisation (ASAE) circuit 7, which is described in British Patent Specification No. 1,430,547. Next, the equalised signal is compared with a reference threshold level in an Automatic Tracking Threshold Circuit (ATTC) 8. This is a technique which has been used before in bottle inspection apparatus. Briefly, the ATTC 8 provides a threshold level signal which is derived from the sum signal itself so as to accommodate containers whose wall thickness and/or colour density may vary significantly. The threshold signal is effectively a smoothed version of the sum signal which lags the latter and is offset from it by a predetermined amount. Where variations in wall thickness and/or colour density is not a problem, a reference threshold level which is a predetermined function of the vertical position of the scanning beam may be used, as described in British Patent Specification No. 1,430,547. When the equalised B, C, D column sum signal falls below the reference threshold level a reject signal is generated on output 9, which reject signal actuates in known manner, at the appropriate time, a bottle rejection mechanism. It should be noted that if only clear bottles are to be inspected the ASAE circuit 7 may be omitted.

The frame summation and comparison is performed by five separate circuits such as that shown in FIG. 6. The circuits differ essentially only in their connection to the output terminals of the diode matrix. In FIG. 6 the particular combination of diode output signals shown at the left are added in an adder $10_1$ to provide a sum signal on line 11. The sum signal on line 11 thus corresponds to the total light received by the diodes in the shaded boxes of FIG. 7A, as can be established by inspection. It will be seen that this includes not merely one but a plurality of adjacent $5 \times 5$ frames. However, this is immaterial as a linear fold pattern will normally only extend into one frame and the contributions from the other frames will be zero. Even if a pattern does extend into two frames this will only increase the sensitivity of detection. The sum signal on 11 is next passed on to an ASAE circuit 12 (which may be omitted when only clear glass containers are inspected) and then to a comparator 13 where the equalised sum signal is compared with a reference threshold level applied at 14. When the sum signal exceeds the threshold level a signal $\Sigma 1$ is generated on output 15. Under appropriate circumstances, when one of the frames of 7A is centred on the current nominal box X in the C column, the signal $\Sigma 1$ is treated as a reject signal.

The other four frame summation and comparison circuits are the same as that shown in FIG. 6, but have a different combination of inputs to the adder in each case. The adders of these other four circuits are identified by $10_2$, $10_3$, $10_4$ and $10_5$ respectively, and the table in FIG. 6A shows the respective combination of inputs applied to each adder. The output signals generated in each case on the respective line 15 when the threshold level is exceeded are identified by $\Sigma 2$, $\Sigma 3$, $\Sigma 4$ and $\Sigma 5$ respectively as indicated at the bottom of the table. By inspection of the various figures it will be seen that the particular frames summed by the adders $10_2$, $10_3$, $10_4$ and $10_5$ are shown shaded in FIGS. 7B to 7E respectively.

In order to detect the existence of a linear pattern corresponding to a fold at a particular scanning position, and not to detect a pattern corresponding to an acceptable bottle, it is necessary to examine the output 15 only of that frame summation and comparison circuit which corresponds to a frame centred on the current nominal box X in the centre C column. Thus, referring to FIGS. 7A to 7E, when the current nominal box X is C31, C32, C33, C34, etc the output 15 of the circuit including adder $10_1$ is used. Similarly, when the current nominal box X is C51, C52, C53, etc the output 15 of the circuit including adder $10_3$ is used. A circuit for selecting the output 15 of the appropriate summation and comparison circuit as the nominal box X travels down the matrix is shown in FIG. 8.

Each of the signals C1 to C5 from the diode matrix is individually compared, if necessary after ASAE compensation in circuits 16, in a respective comparator 17 with a reference level. When the reference level is exceeded by the input C signal in any particular case the respective comparator 17 provides an output signal on 18 which opens an AND gate 19. The reference level is set to correspond to greater than 50% of the maximum light which can fall on the screen 1 in the absence of occlusions so that only one comparator 17 can provide an output, and thus only one AND gate be opened, at any one time. The other input to each AND gate 19 is derived from the output 15 of a respective frame summation and comparator circuit, as shown. If a $\Sigma$ signal appears at the input of the particular AND gate 19 which is currently open this is passed through the AND gate to the output 20 and thence through an OR gate 21 to provide a reject signal on 22. Any $\Sigma$ signals at the inputs of the other AND gates are not passed and cannot provide a reject signal. By inspection it will be seen that this arrangement provides that for any nominal box X in the C column only the $\Sigma$ output (if any) is passed from that frame summation and comparator circuit corresponding to a $5 \times 5$ frame centred on the nominal box X. Thus the effect is that as the scanning beam scans down the C column of the matrix box by box a $5 \times 5$ frame centred on the current box is stepped down the matrix in synchronism with the beam.

If the total light falling on the current nominal box X does not exceed the threshold set by the comparator 17, clearly the output of the surrounding frame will effectively not be examined, since the associated AND gate will remain closed. However, this will normally only occur through the presence of an occlusive fault or a gross deformation of the bottle shifting the beam as a whole away from the centre column, and in either case this will itself generate a reject signal as a result of the drop in the B,C,D column sum signal, so that examination of the surrounding frame is not necessary.

The reject signals on 22 may be used to actuate the bottle rejection mechanism in the same way as the signal on 9 (FIG. 5). However, it can happen that some minor refractive faults other than a fold or the like can provide a reject signal from one of the frame summation and comparison circuits, for example a small bubble in the glass (mico-bubble). We do not wish to reject a bottle merely on the basis of a small bubble, and to distinguish between a fold and a small bubble we use the fact that the latter has much smaller dimensions than the fold, so that the bubble will give a reject signal during only one or two consecutive vertical scans, whereas a fold being of much larger dimensions will normally give a reject signal for a larger number of consecutive vertical scans. Thus the reject signals on 22 are preferably passed to an inhibit reject circuit 23 which is basically a counter arranged to provide a reject signal on 24 only when at least one reject signal appears on 22 during each of a predetermined minimum number of consecutive vertical scans. Finally, the reject signals on 24 and on 9 (FIG. 5) are ORed together so that either will actuate the bottle rejection mechanism mentioned earlier.

Although the above has dealt predominantly with the detection of non-occlusive refractive faults in the form of folds, the frame is also capable of detecting light patterns of other than linear form. For example, certain non-occlusive faults other than folds may produce patterns in the form of a circle, rectangle or triangle. These patterns are also capable of being detected by the frame, if they extend into the frame. If they do not extend into the frame, and if it is nevertheless desired to detect them, this could be done by examining any other suitable pattern of boxes surrounding the current nominal box X. This latter technique is more applicable to the case where a larger diode matrix is used, as described below. However, we have found that the 5×5 frame described above is adequate to detect most of the undesired non-occlusive refractive faults which are encountered in practice.

Furthermore it should be pointed out that the use of a matrix 5 diodes wide is a convenience based upon emperical experiments with certain containers of fairly simple symmetrical shape. Containers of more complex shape may require more sophisticated pattern analysis, and for this purpose it may be necessary to use a matrix having many more diodes across its width and to vary the size and shape of the frames or the like as a function of the vertical position of the scan. This could readily be achieved by appropriate electronic processing circuitry which would, however, of necessity be more complex than that described above.

The principles may also be extended to deal with the same range of defects in sheet glass, plastics, etc. In such case the sheet of material is moved continuously past the scanning beam in its longitudinal direction and is repeatedly scanned by the beam across its width.

We claim:

1. In an apparatus for detecting the presence of faults in an article of translucent material, the apparatus comprising means for generating a spot beam of light and causing it to repeatedly scan in a first direction, means for transporting the translucent material of the article past the spot beam of light in a second direction non-parallel to the first direction so that the surface of the translucent material is repeatedly scanned by the beam in a direction non-parallel to the direction of motion of the material, and a light collection apparatus arranged to receive light from the beam after passing through the translucent material, the improvement wherein the light collection apparatus comprises a light-diffusing screen having a front surface positioned to receive light from the translucent material and a rear surface facing a matrix of photosensitive devices each arranged to provide an electric output signal dependent upon the amount of light emerging substantially only from the rear surface of a respective elemental area of the screen, the apparatus further comprising electrical circuit means for detecting substantially non-occlusive refractive faults in the article by selectively examining different combinations of the output signals of the photosensitive devices in dependence upon the position of the beam.

2. An apparatus as claimed in claim 1, wherein the article is a translucent container, and wherein the means for transporting the translucent material of the article past the spot beam of light comprises means for rotating the container, the said first direction being parallel to the axis of rotation of the container.

3. In an apparatus for detecting the presence of faults in translucent containers, the apparatus comprising a scanning zone, means for rotating a translucent container within the scanning zone, means for generating a spot beam of light and causing it to repeatedly scan a container in the scanning zone in a direction parallel to the axis of rotation of the container, and a light collection apparatus arranged to receive light from the beam after passing through the container, the improvement wherein the light collection apparatus comprises a light-diffusing screen having a front surface facing in a direction to receive light from the scanning zone and a rear surface facing a matrix of photosensitive devices each arranged to provide an electric output signal dependent upon the amount of light emerging substantially only from the rear surface of a respective elemental area of the screen, the apparatus further including electrical circuit means for detecting substantially non-occlusive refractive faults in the container by selectively examining different combinations of the output signals of the photosensitive devices in dependence upon the position of the beam.

4. Apparatus as claimed in claim 3, wherein the matrix of photosensitive devices is a rectangular matrix with one of the major axes thereof arranged parallel to the axis of rotation of the container.

5. Apparatus as claimed in claim 4, wherein the light collector includes a rectangular grid of thin walls sandwiched between the screen and the matrix so as to define a plurality of boxes with a respective photosensitive device located at the rear of each box, each box in turn defining the respective elemental area of the screen from which the associated photosensitive device receives light.

6. Apparatus as claimed in claim 3, wherein in use of the apparatus the spot beam of light, after passing through the container, nominally follows a predetermined path across the screen falling predominately upon a predetermined succession of adjacent elemental areas thereof, and wherein in order to detect substantially non-occlusive refractive faults the electrical circuit means comprises means to examine the output signals of a plurality of photosensitive devices associated with a set of elemental areas bearing a predetermined positional relationship to that elemental area of the predetermined succession upon which the beam predominantly falls at any instant.

7. Apparatus as claimed in claim 6, wherein the said set of elemental areas constitutes a frame of such areas surrounding at a distance that elemental area upon which the beam falls at any instant.

8. Apparatus as claimed in claim 7, wherein the examination means comprises means for deriving a signal related to the sum of the output signals of the photosensitive devices associated with the frame, means for comparing the sum-related signal with a threshold level, and means for generating a fault-indicating signal when the sum-related signal exceeds the threshold level.

9. Apparatus as claimed in claim 8, further comprising a container reject mechanism actuated by a reject signal and means for generating a reject signal upon the occurrence of a fault-indicating signal during each of a predetermined number of individual consecutive scans of the container.

10. Apparatus as claimed in claim 5, wherein in use of the apparatus the spot beam of light, after passing through the container, nominally follows a predetermined path across the screen falling predominately upon a predetermined succession of adjacent elemental areas thereof, and wherein in order to detect substantially non-occlusive refractive faults the electrical circuit means comprises means to examine the output signals of a plurality of photosensitive devices associated with a set of elemental areas bearing a predetermined positional relationship to that elemental area of the predetermined succession upon which the beam predominately falls at any instant.

11. Apparatus as claimed in claim 6, wherein in order to detect occlusive faults the electrical circuit means further comprises means to derive a signal related to the sum of the output signals of the photosensitive devices associated with a field of immediately adjacent elemental areas surrounding and including that elemental area upon which the beam predominantly falls at any instant, and means to compare the sum-related signal with a threshold level.

* * * * *